United States Patent
Konya (10) Patent No.: US 8,540,647 B2
(45) Date of Patent: Sep. 24, 2013

(54) LANCING DEVICE

(75) Inventor: Ahmet Konya, Waldsee (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1026 days.

(21) Appl. No.: 12/501,760

(22) Filed: Jul. 13, 2009

(65) Prior Publication Data

US 2009/0287116 A1 Nov. 19, 2009

Related U.S. Application Data (63) Continuation of application No. PCT/EP2007/011469, filed on Dec. 29, 2007.

(30) Foreign Application Priority Data

Jan. 13, 2007 (EP) .................................... 07000658
Aug. 1, 2007 (EP) .................................... 07015132

(51) Int. Cl.
   *A61B 5/00* (2006.01)
   *A61B 17/14* (2006.01)
   *A61B 17/32* (2006.01)
   *B65D 81/00* (2006.01)

(52) U.S. Cl.
   USPC ............ 600/583; 606/181; 606/182; 600/584

(58) Field of Classification Search
   USPC .......................... 600/583, 584; 606/181, 182
   See application file for complete search history.

(56) References Cited

U.S. PATENT DOCUMENTS

| 4,709,280 | A | 11/1987 | Delacou |
| 5,609,823 | A | 3/1997 | Harttig et al. |
| 7,481,777 | B2 | 1/2009 | Chan et al. |
| 2003/0083686 | A1 | 5/2003 | Freeman et al. |

(Continued)

FOREIGN PATENT DOCUMENTS

| DE | 28 03 345 B1 | 6/1979 |
| EP | 1 714 613 A1 | 10/2006 |
| WO | WO 2005/107596 A2 | 11/2005 |
| WO | WO 2008/083844 A1 | 7/2008 |

OTHER PUBLICATIONS

International Patent Application PCT/EP2007/011469 English Translation of International Preliminary Report on Patentability mailed Aug. 13, 2009.
DE 28 03 345 B1 English Language Translation.

(Continued)

*Primary Examiner* — Rene Towa
*Assistant Examiner* — Adam Eiseman
(74) *Attorney, Agent, or Firm* — Woodard, Emhardt, Moriarty, McNett & Henry LLP (57) ABSTRACT

The invention relates to a lancing system for collecting samples of a body liquid having a receptacle for accommodating a lancet supply strip with a plurality of lancets, arranged transversely to the lengthwise direction of the lancet supply strip, a feed mechanism for transporting a lancet supply strip, placed in the receptacle, to move the lancets of the lancet supply strip one after the other to a puncturing position, and a lancing drive for causing a lancet, which occupies a puncturing position, to perform a puncturing movement. The lancing system is characterized by a bending mechanism for bending a section of the lancet supply strip in lengthwise direction of the lancet supply strip and for thereby separating a lancet tip of a lancet from the lancet supply strip for a puncturing action.

28 Claims, 12 Drawing Sheets

(56) References Cited

U.S. PATENT DOCUMENTS

| | | |
|---|---|---|
| 2003/0199789 A1 | 10/2003 | Boecker et al. |
| 2003/0199906 A1 | 10/2003 | Boecker et al. |
| 2003/0211619 A1* | 11/2003 | Olson et al. ............ 436/44 |
| 2005/0036909 A1* | 2/2005 | Erickson et al. ............ 422/61 |
| 2005/0245845 A1 | 11/2005 | Roe et al. |
| 2005/0245954 A1 | 11/2005 | Roe et al. |
| 2006/0247555 A1 | 11/2006 | Harttig |
| 2007/0038150 A1* | 2/2007 | Calasso et al. ............ 600/583 |
| 2007/0173740 A1* | 7/2007 | Chan et al. ............ 600/583 |
| 2008/0103415 A1 | 5/2008 | Roe et al. |
| 2008/0269791 A1* | 10/2008 | Hoenes et al. ............ 606/181 |

OTHER PUBLICATIONS

International Patent Application PCT/EP2007/011469 International Search Report mailed Mar. 25, 2008.

U.S. Appl. No. 12/394,076, filed Feb. 27, 2009 to Konya et al.

* cited by examiner

LANCING DEVICE

REFERENCE

This application is a continuation of PCT/EP2007/011469 filed Dec. 29, 2007 which is based on and claims priority to European Patent Application No. EP 07000658.0 filed Jan. 13, 2007 and European Patent Application No. EP 07015132.9 filed Aug. 1, 2007, which are hereby incorporated by reference.

FIELD

This disclosure relates to a lancing device for collecting samples of a body liquid, having a receptacle intended to hold a lancet supply strip with a plurality of lancets, arranged transversely to the lengthwise direction of the lancet supply strip, and provided with a lancet tip for producing a puncture wound, a feed mechanism for transporting a lancet supply strip placed in the receptacle to move the lancets of the lancet supply strip one after the other to a puncturing position and a lancing drive for causing a lancet that occupies a puncturing position to perform a puncturing movement. The disclosure further relates to a lancing system and to a tape cassette with a lancet supply strip for a lancing device, and to a device for separating a lancet tip from a lancet supply strip.

BACKGROUND

Lancing devices and relevant lancet supply strips, containing lancets arranged transversely to the lengthwise direction of the lancet supply strip, have been known, for example, from US 2003/0199906 A1 and from DE 2803345 B1. The lancet supply strips described in those applications comprise a flexible carrier on which the lancets are arranged and a sterility protection that covers the lancets. The sterility protection of the known lancet supply strips is a film that must be torn off before the lancets can be used for a puncturing action. For removing the sterility protection, the known lancing systems require considerable technical input.

SUMMARY

The invention therefore has for its object to show an inexpensive way in which lancets of a lancet supply strip can be presented ready for puncturing in a lancing device of the before-mentioned kind.

The invention achieves that object by a bending mechanism for bending a section of the lancet supply strip in lengthwise direction of the lancet supply strip and for thereby separating a lancet tip of a lancet from the lancet supply strip for a puncturing action.

The bending mechanism according to the invention may be attached to a lancing device. There is, however, also the possibility, specifically, to attach the bending mechanism to a tape cassette which is placed in a receptacle of a lancing device for use. A cassette and a lancing device, in which the strip cassette is placed for use, form together a lancing system.

However, a lancing device or lancing system according to the invention can be realized also without exchangeable cassettes in which case an exchange of the lancet supply strip is not envisaged and the lancing device or the lancing system is regarded as a disposable article and is discarded when all lancets of the lancet supply strip have been used.

For purposes of the present application, the term lancet tip is used to describe the forward end of a lancet by which puncturing is to be affected.

When a lancet supply strip, comprising a plurality of lancets arranged transversely to the lengthwise direction of the lancet supply strip, is folded or bent in lengthwise direction, the orientation of a lancet in the bent section of the lancet supply strip is largely retained. With the result that the tip of the lancet is lifted off the supply strip and breaks through a sterility protection or a carrier layer. The lancet tip of a lancet can be separated in this way from the lancet supply strip, in preparation of a puncturing action, so that the lancet is then ready for puncturing. There is no need for a lancet to be fully separated from a lancet supply strip by the bending movement. It is sufficient to have the lancet tip, which will penetrate the skin of a body area to which the lancing device is applied, lifted off the lancet supply strip by the bending movement. The bending movement causes a forward lancet portion, including the lancet tip, to be separated from the lancet supply strip.

A lancing device according to the invention and a lancet supply strip equipped with a plurality of lancets arranged transversely to the lengthwise direction of the lancet supply strip form together a lancing system. Another aspect of the invention relates to a method for separating a lancet tip from a lancet supply strip, where the lancet supply strip is bent in lengthwise direction so that the lancet tip is lifted off the lancet supply strip, bending of the strip being effected using a bending mechanism arranged in a lancing device. Preferably, bending of the strip is effected by the bending mechanism acting on a longitudinal edge of the lancet supply strip.

The lancet supply strip of a lancing system according to the invention may be designed, for example, similar to the lancet supply strip known from US Pat. Pub. No. 2003/0199906 A1 or from German Patent No. DE 2803345 B1 and may comprise a flexible carrier layer on which the lancets are arranged, and a sterility protection that covers the lancets. The sterility protection may consist, for example, of a film, especially of a film made of a plastic material or paper, or of a silicon layer. Another possibility to realize the lancet supply strip consists, for example, in arranging the lancets on a carrier strip, made for example of paper, a plastic and/or metal film, and in folding the carrier strip so that the lancet tips will be covered and protected in this way from detrimental environmental influences. In principle, it is also possible to arrange the lancets on a carrier strip which is then wound up so that the lancets will be protected from damaging environmental influences in the lancet supply roll so formed, between the top and the bottom surfaces of the carrier strip.

BRIEF DESCRIPTION OF THE DRAWINGS

Further details and advantages of the invention will be described hereafter with reference to certain embodiments and to the attached drawings. The features described may be made the subject of claims either individually or in any combination. Identical and corresponding components are indicated by the same reference numerals. In the drawings:

DETAILED DESCRIPTION

Figure 1:
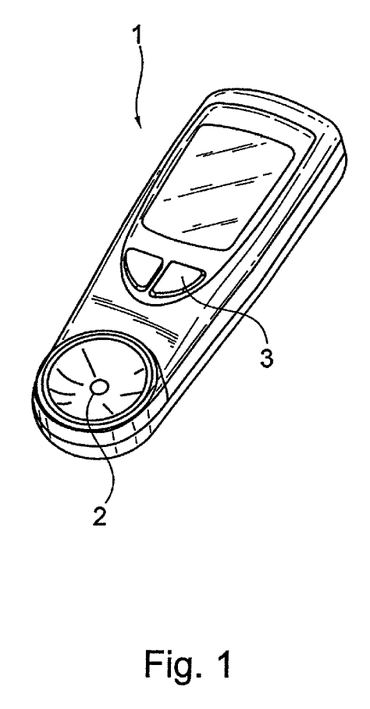
FIG. 1 shows an embodiment of a lancing device according to the invention.

FIG. 1 shows a diagrammatic representation of one embodiment of a lancing device 1 according to the invention intended for collecting a sample of a body liquid. The lancing device 1 has an opening 2 against which a body area is pressed for producing of a puncture wound. Further, the lancing device 1 comprises operating elements 3 in the form of keys and a display 4 in the form of a liquid crystal display intended for displaying examination results. The lancing device 1 is provided with a receptacle (not shown) for a lancet supply strip. The receptacle has an opening that can be closed and is provided at the rear of the embodiment illustrated in FIG. 1.

The lancing device 1 illustrated in FIG. 1, and the lancet supply strip 5 illustrated in FIGS. 2 to 9 form together a lancing system. The lancet supply strip 5 carries a plurality of lancets 6, each arranged transversely to the lengthwise direction of the lancet supply strip 5 and provided with a lancet tip 6a for application of a puncturing wound. FIGS. 2 to 9 show, in a diagrammatic representation, a detail of the interior of the instrument with a lancet supply strip 5 in place, in different operating positions to which reference will be made in the discussion that follows of the operation of the lancing device 1.

Figure 2:
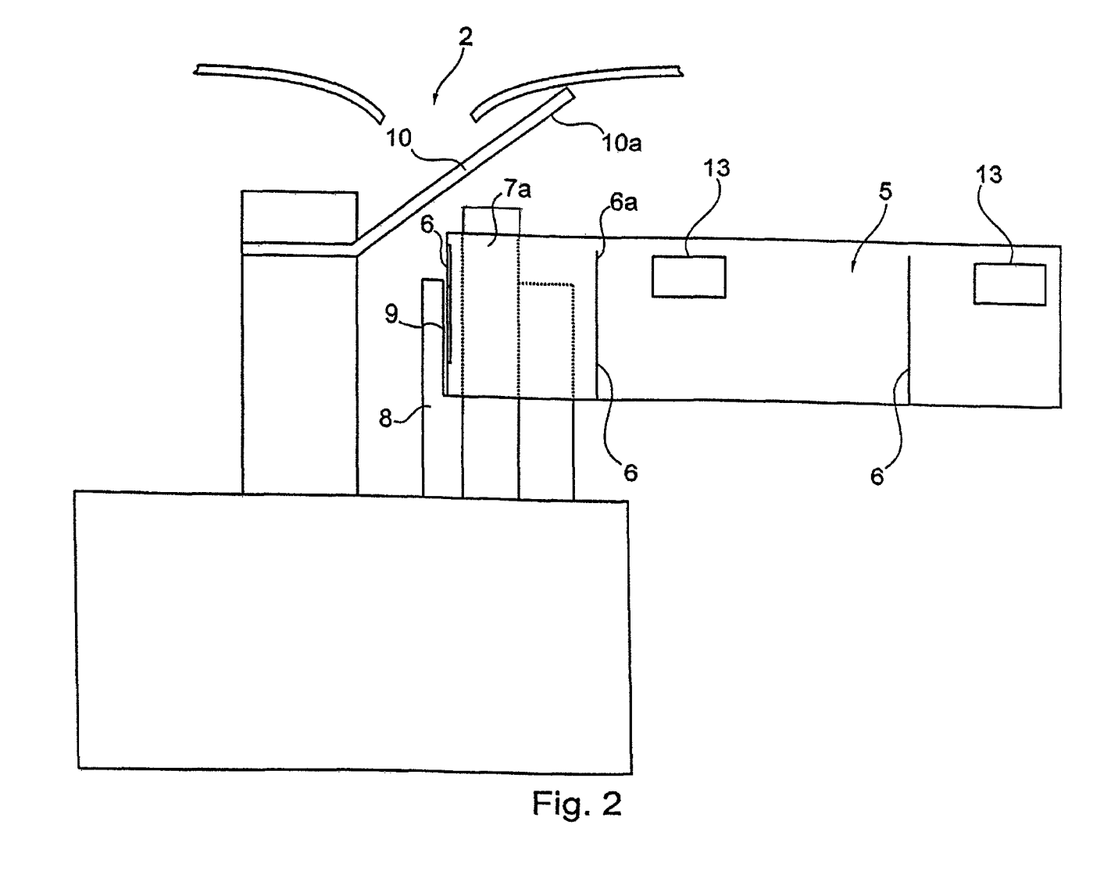
FIG. 2 shows a diagrammatic interior view of the embodiment illustrated in FIG. 1 with a loaded lancet supply strip, prior to bending.
Figure 3:
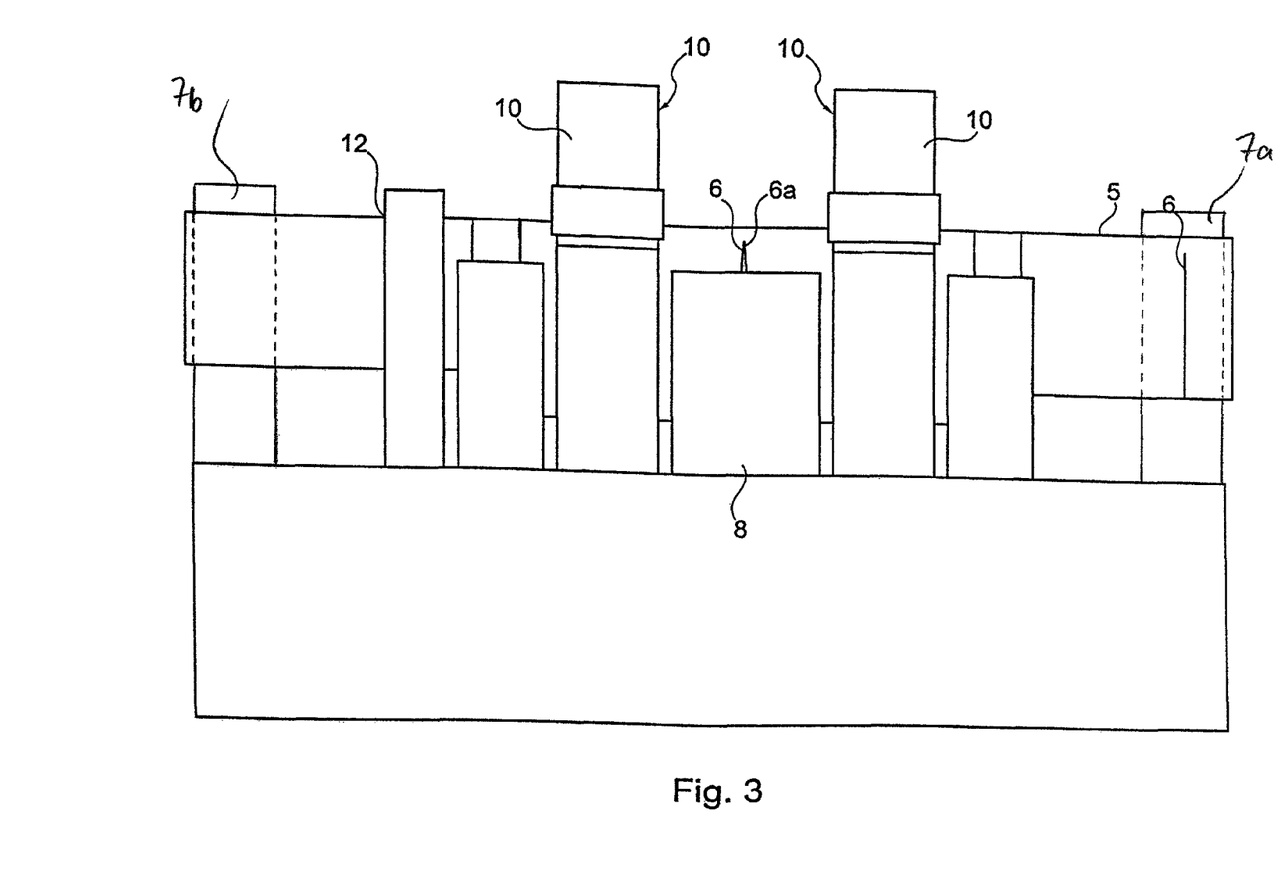
FIG. 3 shows a view turned by 90° relative to FIG. 2.

The lancets 6 of a lancing device 1 placed in the lancing device can be moved to a puncturing position one after the other using a feed mechanism. A lancet 6 that has been moved to the puncturing position has its lancet tip 6a pointing away from the interior of the lancing device 1 in the direction of the instrument opening 2. In FIGS. 2 and 3 the lancet supply strip 5 has been positioned so that a lancet 6 occupies the puncturing position.

The feed mechanism may consist, for example, of a winding mechanism by which a lancet supply strip 5, which may have been placed in the receptacle of the lancing device 1 as a wound-up roll or a fan-folded stack, can be wound up after use and thereby moved in lengthwise direction. The lancet supply strip 5 may be contained, for example, in a tape cassette that is loaded into the lancing device for use.

A lancet 6 that occupies the puncturing position, i.e. that has its tip 6a pointing in the direction of the instrument opening 2, as indicated in FIG. 2, can be driven by the lancing drive 8 to perform a puncturing movement. In the illustrated embodiment, the lancing drive 8 comprises a holder with a slot 9 with the lancet supply strip 5 passed through that slot. For a puncturing operation, the lancing drive 8, together with the holder, are moved in the puncturing direction whereby the section of the lancet supply strip 5 present in the slot 9 is accelerated, together with the lancet 6 that occupies the puncturing position, so that the tip 6a of the lancet 6 will puncture a body area that is pressed against the instrument opening 2. During the puncturing operation, the lancet 6 remains connected with the lancet supply strip 5 as only the lancet tip 6a is lifted off the lancet supply strip 5 during the bending movement.

In the simplest of all cases, a puncturing movement of the holder of the lancing drive 8 may be transmitted to the lancet supply strip 5 by an arrangement where the longitudinal edge of the lancet supply strip 5, facing away from the lancet tip 6a of the lancet supply strip 5, rests on the bottom of the slot 9 in the holder. Improved transmission of a puncturing and a reverse movement of the lancing drive 8 to the lancet supply strip 5 can be achieved when the slot 9 is contracted by a suitable mechanical system once a lancet 6 occupies the puncturing position so that the lancet strip 5 is clamped in the slot 9. Upon completion of the reverse movement, the slot 9 is then widened again so that the lancet supply strip 5 can be advanced by the feed mechanism.

In the illustrated embodiment, the lancet supply strip 5 is guided by a guide element 7a in the form of a guide pulley that can be seen in front of the slot 9, in the feed direction. It is possible in this way to facilitate the movement of the lancet supply strip 5 through the slot 9 and to prevent the lancet supply strip 5 from being blocked in the slot 9. Arranged behind the slot 9, in the feed direction, is a guide element 7b in the form of a guide pulley which, just as the guide pulley 7a, contributes toward feeding the lancet supply strip 5 through the slot 9. The guide elements are not shown in FIGS. 4, 5, 8 and 9 for the sake of clarity.

The tips 6a of the lancets 6 of the loaded lancet supply strip 5 are enclosed by a sterility protection, consisting—in the illustrated embodiment—of a plastic film, that covers the lancets 6 arranged on a flexible carrier strip. Just as the sterility protection, the carrier strip may also be made from plastic, paper or metal.

Figure 4:
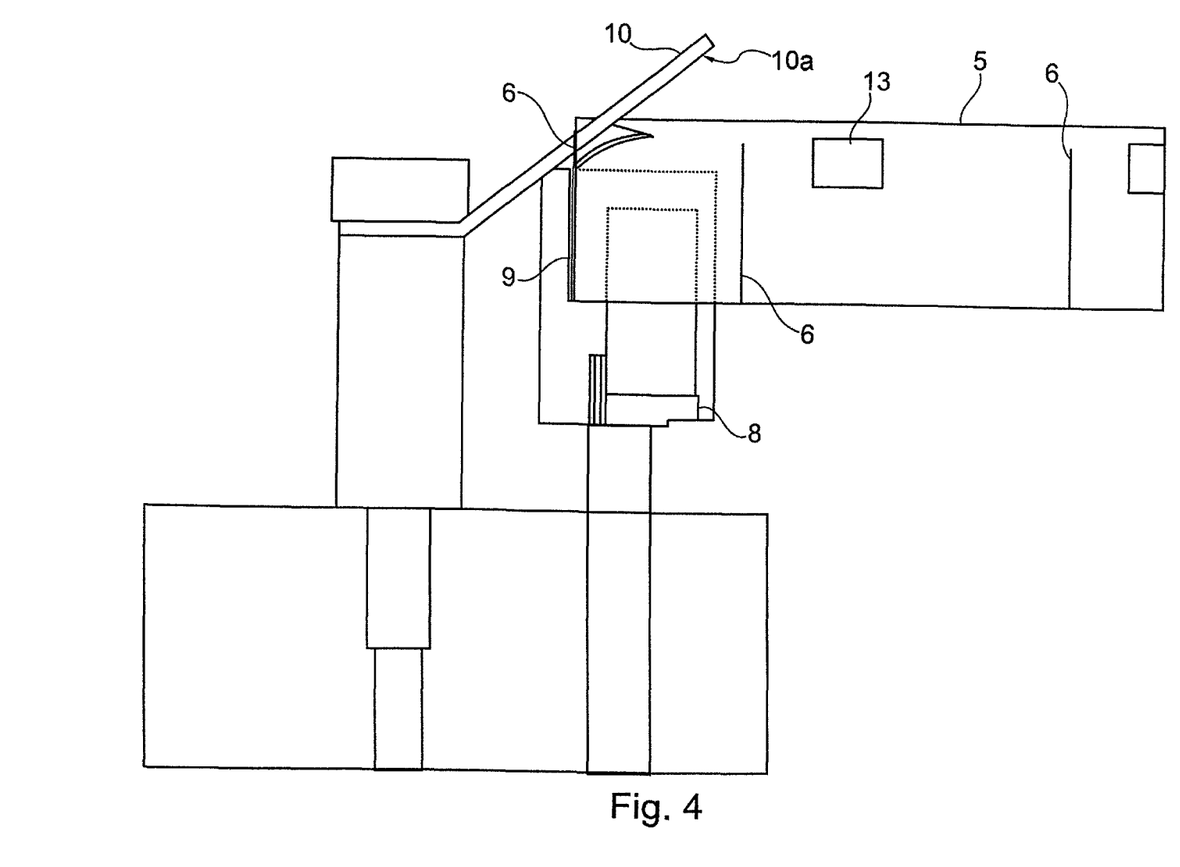
FIG. 4 shows a representation similar to that of FIG. 2, after bending of the lancet supply strip.
Figure 5:
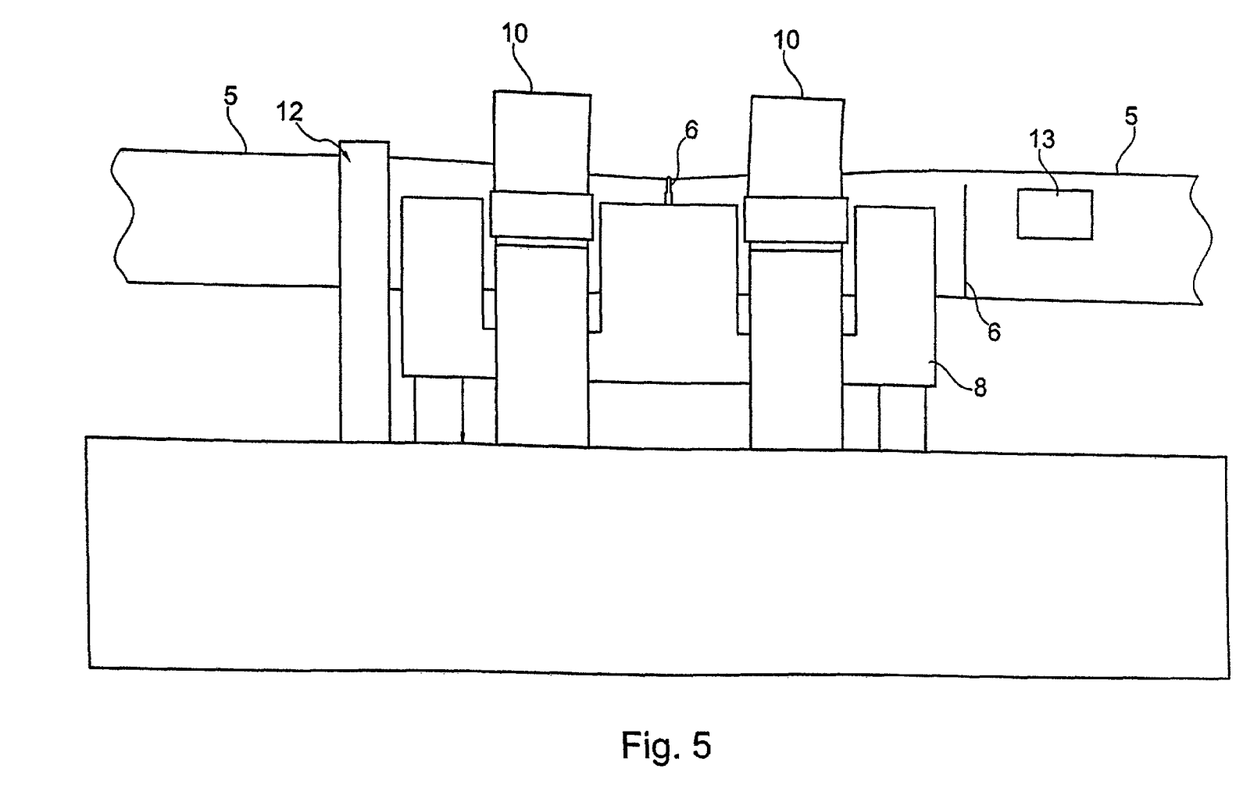
FIG. 5 shows a view turned by 90° relative to FIG. 4.

For separating a lancet tip 6a of a lancet 6 from the lancet supply strip 5, the lancet supply strip 5 is bent by a bending mechanism 10 in lengthwise direction of the lancet supply strip 5. To this end, the lancet supply strip 5 is moved by the lancing drive 8 in the puncturing direction so that the forward longitudinal edge, viewed in the puncturing direction, of the lancet supply strip 5 abuts against the bending mechanism 10. FIGS. 4 and 5 show a section of the lancet supply strip 5 bent in lengthwise direction, with the lancing drive 8 displaced in the puncturing direction. As can be seen, the lengthwise bending movement has caused the forward longitudinal edge of the lancet supply strip 5, viewed in the puncturing direction, to be bent toward the rear longitudinal edge, viewed in the puncturing direction, and has somewhat reduced the distance between the two longitudinal edges compared with the unbent condition.

When the lancet supply strip 5 is bent in this way, the lancet 6 retains its orientation, thereby tearing through the sterility protection by which it is covered, in the illustrated embodiment a cover film, or the flexible carrier strip. The lancet tip 6a is lifted off the lancet supply strip 5 during the bending process, being thereby separated from the strip, so that the lancet tip 6a can puncture a body area that is pressed against the instrument opening 2 for collecting a sample of a body liquid.

For bending the lancet supply strip 5, the bending mechanism 10 acts on a longitudinal edge of the lancet supply strip 5. In the illustrated embodiment, the lancet supply strip 5 is moved from the position illustrated in FIGS. 2 and 3 in the puncturing direction until it reaches the position illustrated in FIGS. 4 and 5 in which a section of the lancet supply strip 5 is bent in lengthwise direction because a longitudinal edge of the lancet supply strip 5 is pressed against the bending mechanism 10 by the lancet drive 8. Bending the lancet supply strip 5 in lengthwise direction and, accordingly, preparing a lancet 6 for a puncturing action, is effected during an early phase of the puncturing movement in the illustrated embodiment. This permits the risk of contamination of the lancet tip 6a, which generally exists after separation of the lancet tip 6a from the lancet supply strip 5 because the sterility protection has then been broken, to be minimized.

In principle, it would be sufficient to act on a longitudinal edge of the lancet supply strip 5 at a single point only, for example at a point beside the lancet 6. Bending can be improved, however, when the bending mechanism 10 acts on two points, spaced one from the other, of that longitudinal edge of the lancet supply strip 5 which faces the lancet tip 6a so that the section of the strip that is bent between those two points has no contact with the bending mechanism 10 and a lancet tip 6a present in that section of the lancet supply strip 5 does not get into contact with the bending mechanism 10. This can be achieved, for example, by providing the bending mechanism 10 with a slot. In that case, a lancet tip 6a can retain its orientation during bending of the lancet supply strip 5 and can project into the slot. In FIG. 5, the bending mechanism 10 can be seen to press on a longitudinal edge of the lancet supply strip 5, at the left and right sides of the lancet 6.

In the illustrated embodiment, the bending mechanism 10 has two bending surfaces 10a extending at a distance one from the other, obliquely to the puncturing direction. As can be seen especially in FIGS. 2 and 4, such bending surfaces 10a may be configured in the form of a fork, for example as webs, and may extend along a straight line, as is the case in the illustrated embodiment. In principle, the bending surfaces 10a may, however, also have a curved shape. It is sufficient if one longitudinal edge of the lancet supply strip 5, being pressed against a bending surface 10a, slides off so that the respective section of the lancet supply strip 5 is bent off in lengthwise direction. When a section of the lancet supply strip 5 is bent in lengthwise direction, a bulged portion will be formed which extends in lengthwise direction and which can be seen in FIGS. 4 and 5.

The embodiment illustrated in FIG. 1 comprises a testing facility 12 for examination of a sample of a body liquid. Such a testing facility 12 may be a photometric testing facility that examines a change in color of a test field containing indicator reagents which cause the test field to change color in response to the particular analyte concentration. For example, the testing facility 12 may be an electrochemical testing facility suited for detecting a measuring current indicative of the analyte concentration. Suitable testing facilities are, for example, integrated in commercially available hand-held analyzers of the kind used, for example, by diabetics for monitoring the sugar content of their blood. In addition to lancets 6, the lancet supply strip 5 also carries test fields 13 so that the described lancing system can be used to collect and to then examine a sample of a body liquid, for example for measuring the glucose content.

The testing facility 12 of the lancing device 1 coacts with a test field 13 of the lancet supply strip 5 to take up a sample of a body liquid leaking from a puncture wound. This process will now be discussed in more detail with reference to FIGS. 6 to 9.

Figure 6:
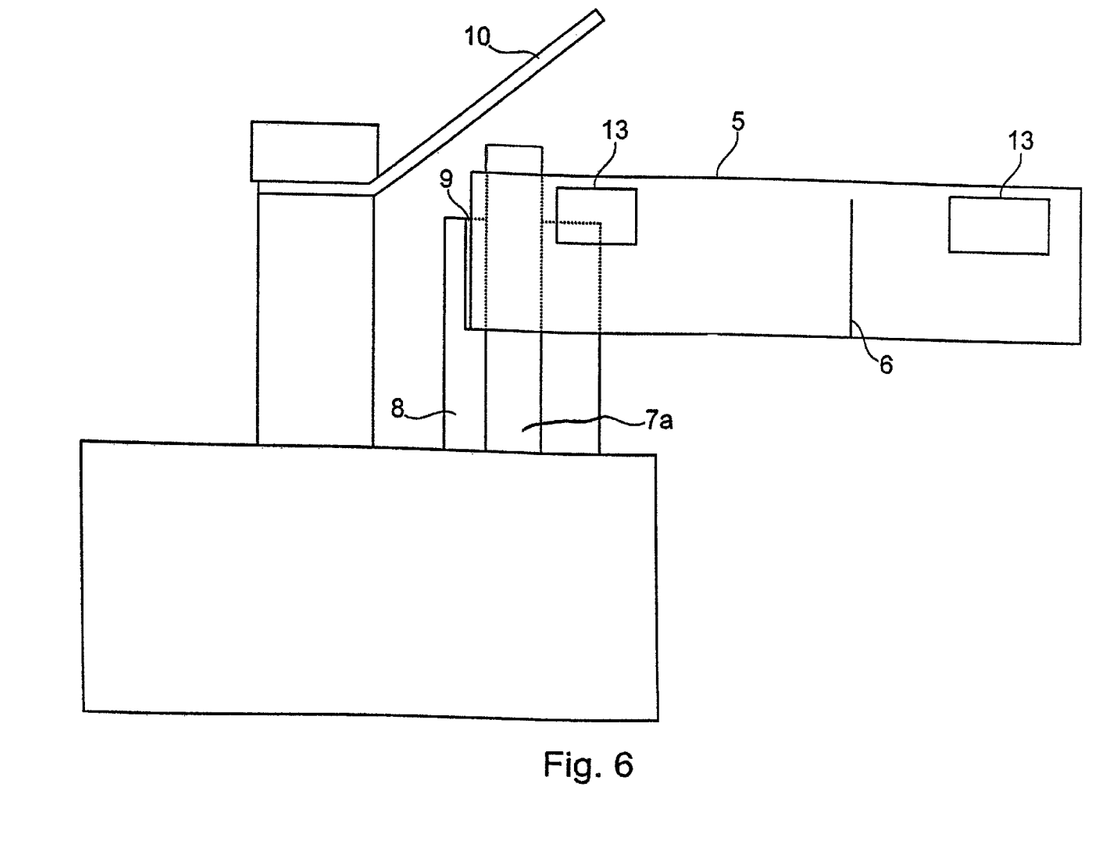
FIG. 6 shows the position of the lancet supply strip relative to the bending mechanism, after a puncturing action.
Figure 7:
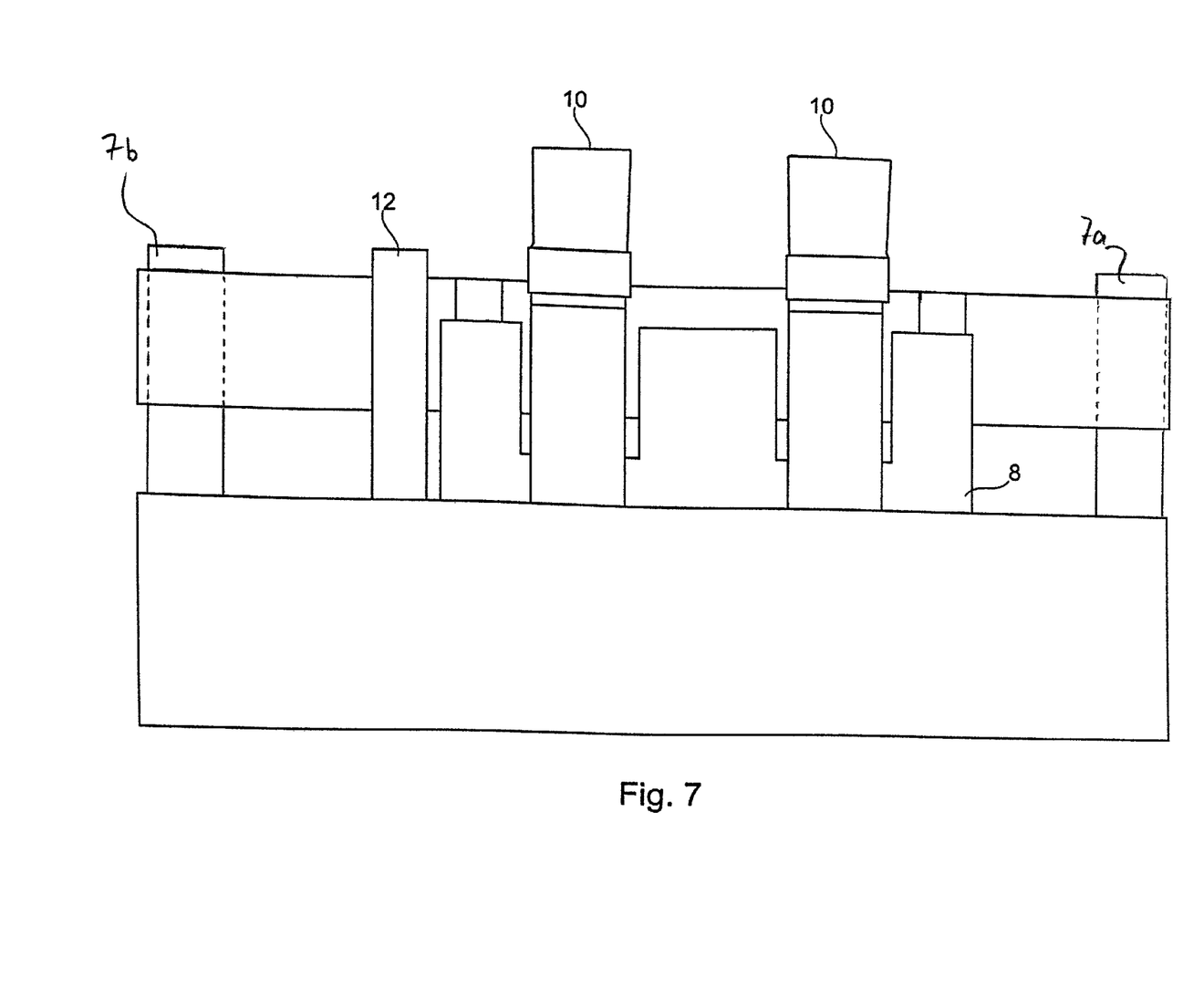
FIG. 7 shows a view turned by 90° relative to FIG. 6.

The action of the bending mechanism 10 on the lancet supply strip 5, beginning with a puncturing movement, is terminated by a subsequent reverse movement by which the lancet drive 8 and the section of the lancet supply strip 5 present in the slot 9 are returned to their initial position illustrated in FIGS. 2 and 6. The lancet supply strip 5 is then no longer pushed against the bending mechanism 10. Following the puncturing action, the action of the bending mechanism 10 on the lancet supply strip 5 is thus interrupted for taking up a sample of a body liquid so that the bent section of the lancet supply strip 5 reassumes its flat condition in which it is illustrated in FIG. 6, for example.

Thereafter, the lancet supply strip 5 is advanced by the feed mechanism to a point where the test field 13 of the lancet supply strip 5 is in alignment with the device opening 2 and a puncture wound that had been produced before in a body area pressed against the instrument opening 2. The lancet supply strip 5 is then advanced again in puncturing direction by the lancing drive 8 and thereby bent once more in lengthwise direction by the bending mechanism 10. As a result of that movement, a partial area of the lancet supply strip 5 is applied to that body area where the puncture wound has been produced. In the illustrated embodiment, the partial area by which the lancet supply strip 5 is applied to the body area is a test field 13. So, the longitudinal edge of the lancet supply strip 5 is again pressed against the bending mechanism 10 during that step.

By providing that a sample of a body liquid is taken up by application of a partial area of the lancet supply strip 5 bent in lengthwise direction, to a body area where a puncturing would has been produced, it is possible with advantage to avoid any contamination of the lancing device. The lancets used and the examined samples of body liquid, and any lancet supply strip used up, can be disposed of together in a hygienic and user-friendly way.

Figure 8:
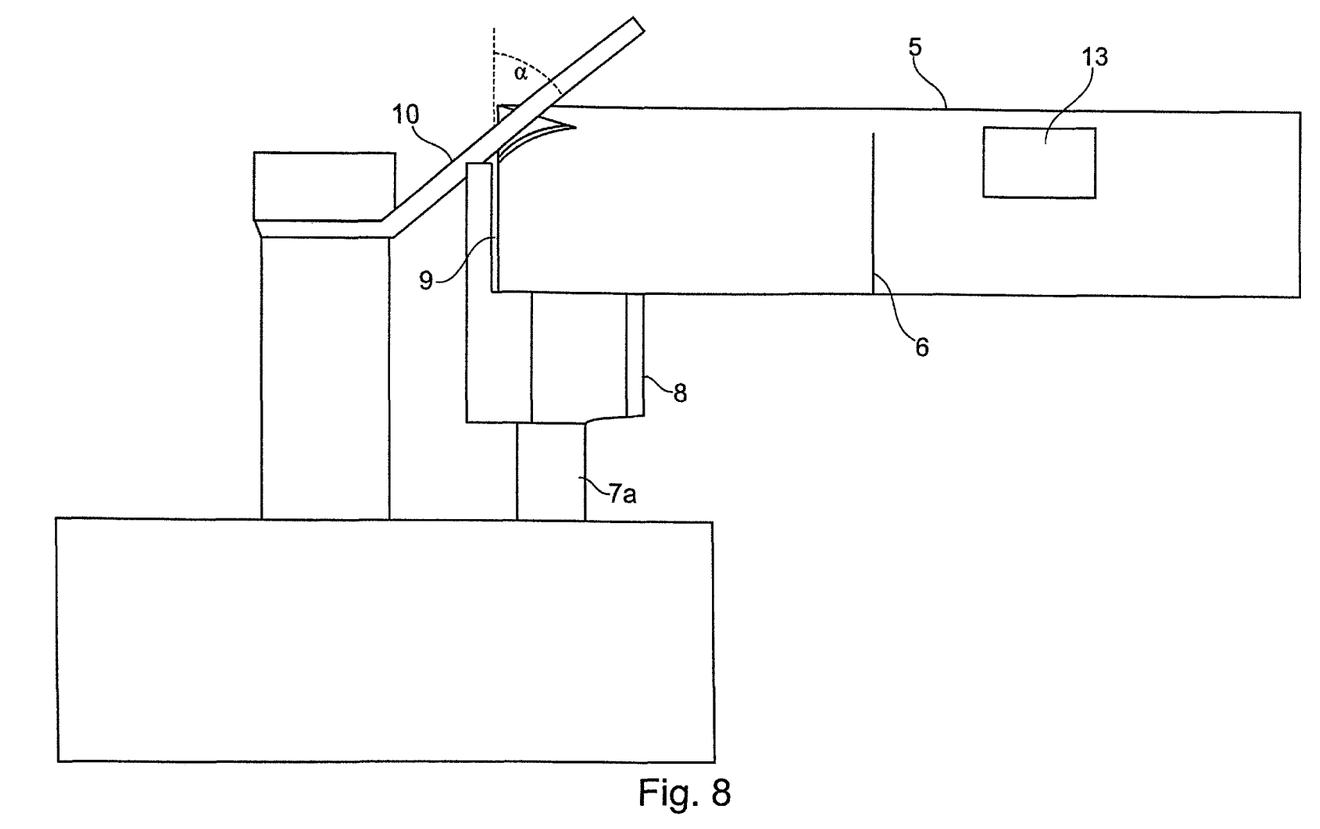
FIG. 8 shows the lancet supply strip in a sample collection position.
Figure 9:
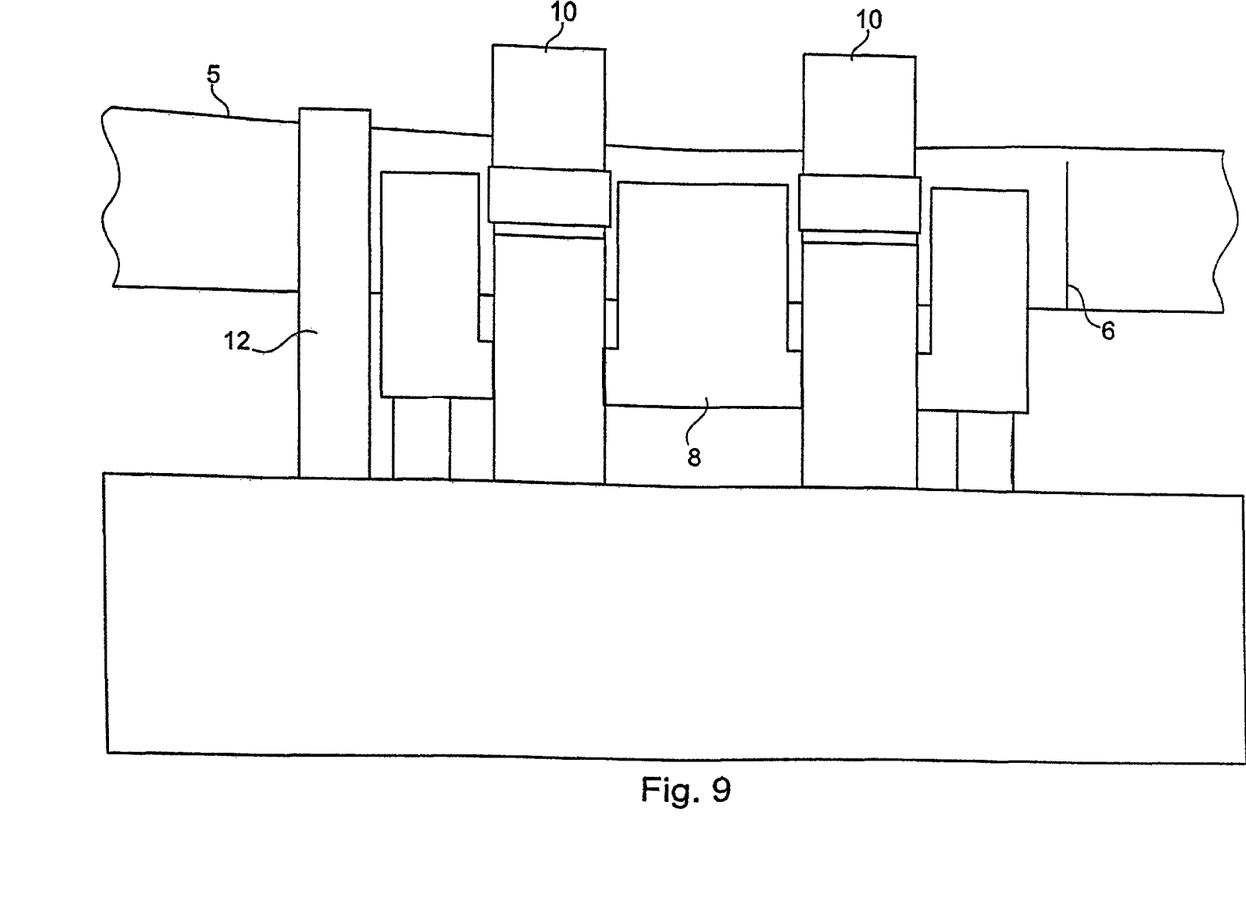
FIG. 9 shows a view turned by 90° relative to FIG. 8.

In the illustrated embodiment, the bending mechanism 10 bends the lancet supply strip 5 in lengthwise direction by an angle α of approximately 45° illustrated in FIG. 8. In the illustrated embodiment, the lancet supply strip is bent by at least 25°, especially at least 30°. For taking up a sample of a body liquid, bending angles of 40° to 90° are particularly favorable in which case an advantageously large partial area of the lancet supply strip 5 can be applied to the body area for taking up a sample of a body liquid.

After a sample of a body liquid has been taken, the lancet supply strip 5 is reversed by the lancing drive 8, i.e. is separated again from the bending mechanism 10 whereby the action of the bending mechanism 10 is interrupted once more so that the bent section of the lancet supply strip returns to its flat condition. Thereafter, the lancet supply strip 5 is advanced by the feed mechanism a further step to move the test field 13, now wetted by the sample of the body liquid, to the testing facility 12. The testing facility 12 then determines, by interaction with the test field 13, an analyte concentration, for example the glucose concentration of the body liquid.

Figure 10:
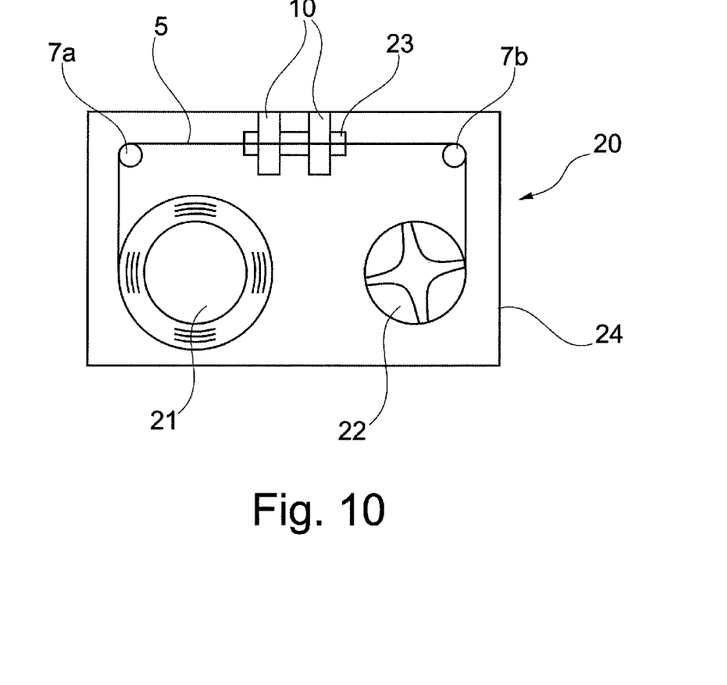
FIG. 10 shows a diagrammatic representation of an embodiment of a strip cassette.

FIG. 10 shows a diagrammatic representation of one embodiment of a tape cassette 20 containing a lancet supply strip 5 that carries a plurality of lancets arranged transversely to the lengthwise direction of the lancet supply strip 5. The cassette is provided with a bending mechanism 10 for bending a section of the lancet supply strip 5 in the lengthwise direction of the lancet supply strip and for separating in this way the lancet tip of a lancet from the lancet supply strip 5 in preparation of a puncturing operation.

Figure 11:
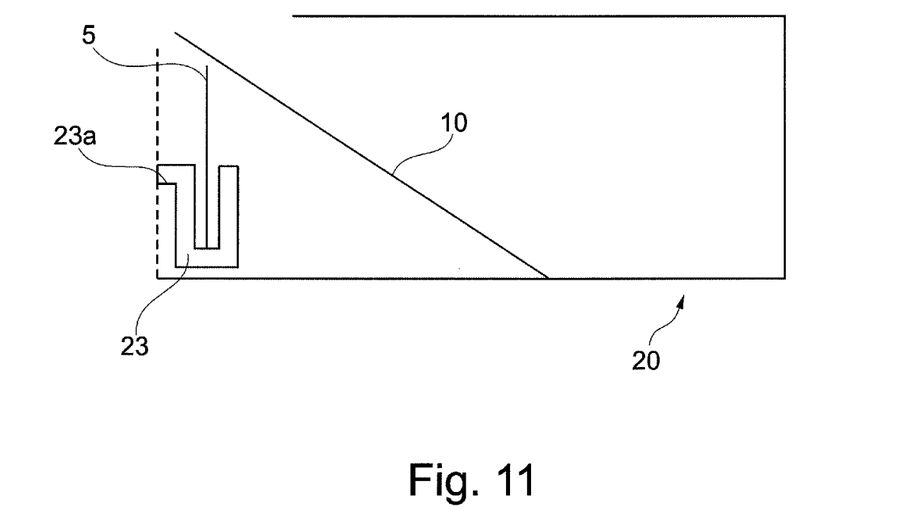
FIG. 11 shows a side view of the embodiment illustrated in FIG. 10.

All that has been said above in relation to the bending mechanism 10 of the embodiment described before with reference to FIGS. 1 to 9 also holds for the embodiment illustrated in FIG. 10. Just as the bending mechanism of the embodiment described above, the bending mechanism 10 is configured in the form of two webs arranged obliquely to the puncturing direction. In the case of the illustrated embodiment the bending mechanism is attached to a frame 24 of the cassette 20, which can be seen best in FIG. 11 showing a diagrammatic side view relative to the representation of FIG. 10.

The frame 24 of the cassette carries a supply roller 21 on which the lancet supply strip with the unused lancets is wound up, and a feed roller 22 on which the used sections of the lancet supply strip 5 are wound up. The feed roller 22 has a central recess with a contour different from a circular shape, in the illustrated embodiment a star-like contour, so that a strip cassette 20, being loaded in a lancing device 1, will engage a driven shaft of the lancing device 1.

In the cassette 20, the lancet supply strip 5 is guided through a coupling head 23 via guide rollers 7a, 7b. As the cassette 20 is loaded in a lancing device 1, the coupling head 23 engages the lancing drive 8 of the lancing device 1 so that the coupling head 23 can be moved in the puncturing direction. In the illustrated embodiment, the coupling head 23 is provided with a coupling element 23a in the form of a pin, for engaging the lancing drive 8 of a lancing device 1. The coupling head 23 is provided with a slot or a groove through which the lancet supply strip 5 is passed. When the coupling head 23 performs a movement of stroke, the lancet supply strip 5 is also moved in the puncturing direction so that its longitudinal edge hits upon the bending mechanism 10 and the lancet supply strip 5 is bent off. During that bending movement of the lancet supply strip 5, the tip of the lancet 6 is lifted off the lancet supply strip 5 for a puncturing action.

Figure 12:
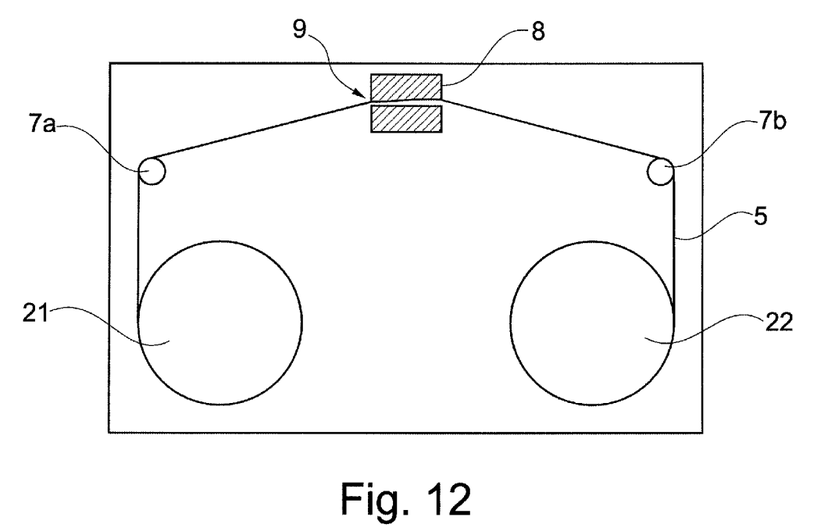
FIG. 12 shows a diagrammatic top view of another embodiment of a lancing device according to the invention.

FIG. 12 shows a diagrammatic top view of another embodiment of a lancing device or a lancing system where the lancet supply strip 5 is bent in lengthwise direction so that a lancet tip of a lancet 6 is lifted off the lancet supply strip 5. In contrast to the embodiments described above, the longitudinal edge of the lancet supply strip 5 it is not acted on at the beginning of the bending movement. Instead, bending is achieved by the fact that during a puncturing movement a higher stress is exerted on the forward longitudinal edge of the lancet supply strip 5 than on its rear longitudinal edge. This will now be explained with reference to FIGS. 12 to 14.

Figure 13:
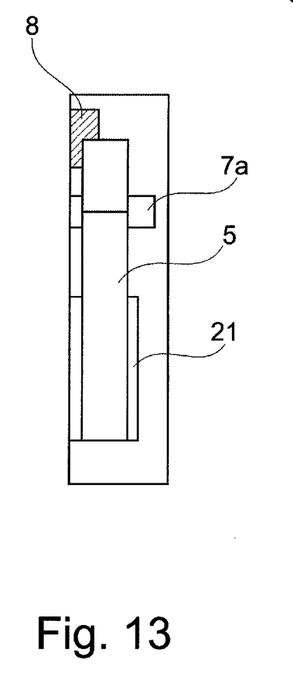
FIG. 13 shows a side view of the representation of FIG. 12, prior to a puncturing movement.
Figure 14:
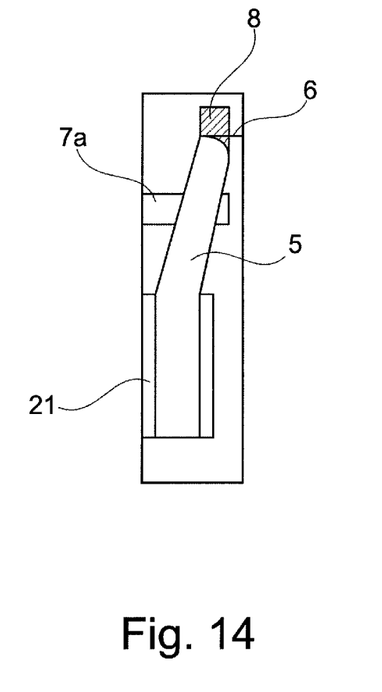
FIG. 14 shows a side view of the representation of FIG. 12, during a puncturing movement.

In the case the embodiment shown in a diagrammatic top view in FIG. 12 and in FIGS. 13 and 14 before and during a puncturing movement the puncturing movement occurs in the direction of the geometric rotary axis of the feed roller 22. Similar to the embodiments described above, a lancet 6 is held in the puncturing position in a holder 8 of the lancet drive together with the section of the lancet supply strip 5 on which it is carried. The holder 8 has a slot 9 through which the lancet supply strip 5 is passed. As in the case of the embodiments discussed before, the holder 8 is arranged between two guide elements 7a, 7b, for example two pins that deflect the lancet supply strip 5, i.e. change its direction of movement, in FIG. 12 by somewhat more than 90°, as the lancet supply strip 5 is guided past the pins. However, in contrast to the embodiments described above, the holder 8, instead of being arranged in alignment with the guide elements 7a, 7b, is arranged offset transversely to the puncturing direction. The section of the lancet supply strip 5 which leads to the holder 8, and the section of the lancet supply strip 5 which leads away from the holder 8 therefore enclose between them an angle of less than 180°.

During a puncturing action the holder 8 moves from its initial position illustrated in FIG. 13 to its position shown in FIG. 14. That movement causes the strip section held in the holder 8 to be moved out of the winding plane in which the lancet supply strip 5 is wound up by the feed roller 22. The offset arrangement between the two guide elements 7a and 7b, transversely to the puncturing direction of the holder 8, now has the effect that the forward longitudinal edge of the lancet supply strip 5, viewed in the puncturing direction, is exposed to a tensile stress during that movement. As a result of that tensile stress, the forward longitudinal edge, viewed in the puncturing direction, bends toward the guide elements 7a, 7b. The bent-over longitudinal edge of the lancet supply strip 5 is indicated by an arrow in FIG. 14. So, bending of the lancet supply strip 5 in lengthwise direction is achieved in the case of the embodiments illustrated in FIGS. 12 to 14 even without any action on the longitudinal edge to be bent.

Accordingly, the bending mechanism of the embodiments illustrated in FIGS. 12 to 14 is designed in that a lancet 6, together with a section of the lancet supply strip 5 on which it is carried, is held in the holder 8 of the lancet drive, the holder being arranged offset transversely to the puncturing direction between two guide elements 7a, 7b, about which the lancet supply strip 5 is guided, and performing a movement in the puncturing direction during a puncturing action.

FIGS. 15 to 18 show another embodiment where, similar to the embodiment described before, longitudinal bending of the lancet supply strip 5 is achieved without any action on the forward longitudinal edge of the lancet supply strip 5, viewed in the puncturing direction.

Figure 15:
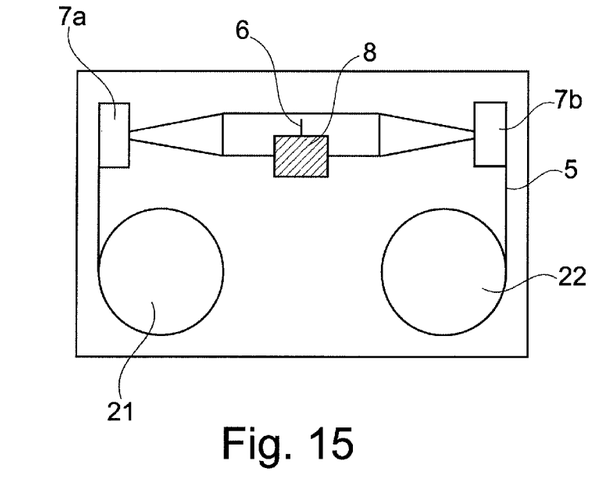
FIG. 15 shows a diagrammatic top view of another embodiment of a lancing device according to the invention, prior to a puncturing movement.
Figure 16:
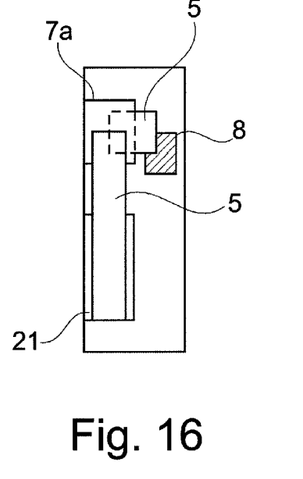
FIG. 16 shows a side view of the representation of FIG. 15, prior to a puncturing movement.
Figure 17:
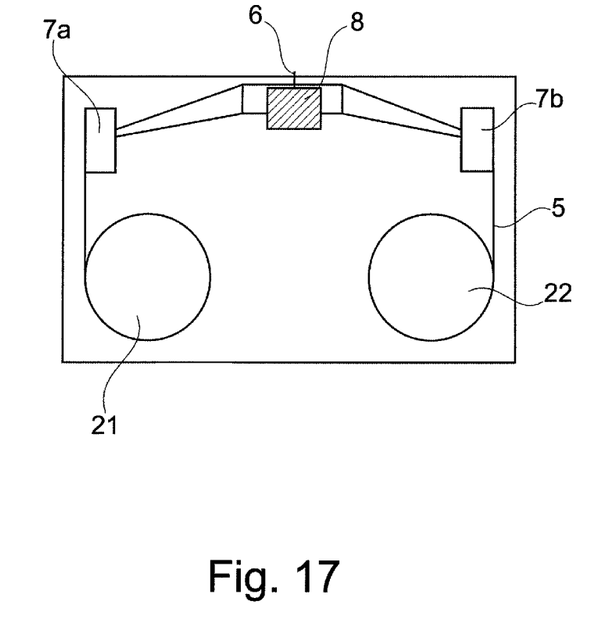
FIG. 17 shows a top view of the embodiment illustrated in FIG. 15, during a puncturing movement.

FIG. 15 shows a diagrammatic top view of a lancing device or a lancing system prior to a puncturing movement. That embodiment differs from the embodiment described above essentially in that the puncturing direction extends transversely to the geometric rotary axis of the feed roller 22. On its way from the supply roller 21 to the holder 8 of the lancing drive, the lancet supply strip 5 therefore is turned by one quarter of a rotation. A further quarter turn follows on the way from the holder 8 to the feed roller 22. As a result, the plane of the lancet supply strip 5 in the holder 8 then extends transversely to the plane of the lancet supply strip 5 in the wound-up condition.

The quarter turn of the lancet supply strip 5 is effected in the illustrated embodiment at the guide elements 7a, 7b past which the lancet supply strip 5 is guided on its way to the feed roller 22, thereby changing its direction of movement, in the illustrated embodiment by approximately 90°. Similar to the embodiment described above, the holder 8 is provided in offset arrangement between the two guide elements 7a, 7b, transversely to the puncturing direction and transversely to an imaginary connection line between the two guide elements 7a, 7b. This can be clearly seen in FIG. 16 where the holder 8 is shown on the right of the supply roller 21 and the guide element 7a, i.e. "above" the two guide elements 7a, 7b in FIG. 15. Therefore, the section of the lancet supply strip 5 that leads to the holder 8 in the transport direction of the strip, and the section of the lancet supply strip 5 that leads away from the holder 8 enclose between them an angle of less than 180° also in the embodiment illustrated in FIGS. 15 to 18.

Figure 18:
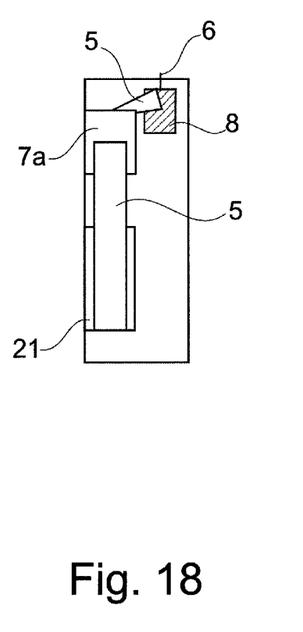
FIG. 18 shows a side view of the embodiment illustrated in FIG. 17, during a puncturing movement.

Just as in the embodiment described with reference to FIGS. 12 to 14, a tensile stress is exerted on the forward longitudinal edge of the lancet supply strip 5, viewed in the puncturing direction, during a puncturing movement of the holder 8 of the embodiment illustrated in FIGS. 15 to 18. The forward longitudinal edge of the lancet supply strip 5 yields to that tensile stress by bending toward the rear longitudinal edge, viewed in the puncturing direction. So, the lancet supply strip 5 is bent in lengthwise direction during a puncturing movement in this embodiment as well so that the lancet tip of a lancet 6, occupying its puncturing position, will be lifted off the lancet supply strip 5. In FIG. 18, an arrow can be seen pointing to the bent-off longitudinal edge of the lancet supply strip 5.

Accordingly, in the embodiment illustrated in FIGS. 15 to 18, the bending mechanism is again characterized by the particular strip-guiding arrangement, i.e. the arrangement of the holder 8 relative to the guide elements 7a, 7b.

Thus, embodiments of the lancing device are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A lancing system for collecting samples of a body liquid comprising:
    a lancet supply strip with a plurality of lancets, arranged transversely to a lengthwise direction of the lancet supply strip;
    a feed mechanism for transporting a lancet supply strip, placed in a receptacle, to move the lancets of the lancet supply strip one after the other to a puncturing position, wherein the feed mechanism is configured to move the lancet supply strip along the lengthwise direction; and
    a lancing drive for causing a lancet, which occupies the puncturing position, to perform a puncturing movement in a direction transverse to the lengthwise direction of the lancet supply strip, said lancing drive being configured for moving the lancet together with the lancet supply strip in a puncturing movement; and
    a bending mechanism for bending a section of the lancet supply strip in lengthwise direction of the lancet supply strip and for thereby separating a lancet tip of a lancet from the lancet supply strip when the lancet is moved together with the lancet supply strip by the lancing drive in the puncturing movement.

2. The lancing system as defined in claim 1, characterized by
    a tape cassette comprising a lancet supply strip with a plurality of lancets arranged transversely to the lengthwise direction of the lancet supply strip; and
    a lancing device having
    a receptacle for accommodating a cassette;
    a feed mechanism for transporting the lancet supply strip of a cassette, placed in the receptacle, to move the lancets of the lancet supply strip one after the other to a puncturing position; and
    a lancing drive for causing a lancet, which occupies a puncturing position, to perform a puncturing movement.

3. The lancing system as defined in claim 1, characterized in that the lancet supply strip comprises test fields for examination of samples of body liquids.

4. The lancing system as defined in claim 1, characterized in that the lancet tips of the lancets of the lancet supply strip are enclosed by a sterility protection which is broken by a lancet tip when a section of the lancet supply strip containing a lancet is bent.

5. The lancing system as defined in claim 1, wherein the bending mechanism is integrated into the lancing drive.

6. The lancing system as defined in claim 5, wherein the lancing drive is configured to move the lancet from a first position wherein the section of the lancet supply strip is in an unbent state to a second position wherein the section of the lancet supply strip is bent in the lengthwise direction to separate the lancet tip from the lancet supply strip.

7. The lancing system as defined in claim 6, wherein the lancing drive is configured to exert higher stress on a forward longitudinal edge of the lancet supply strip than on a rear longitudinal edge of the of lancet supply strip.

8. The lancing system as defined in claim 7, wherein the bending mechanism includes
    two guide elements guiding the lancet supply strip,
    a holder arranged offset transversely to the puncturing direction between the two guide elements, the holder being configured to hold the lancet in the puncturing position, and
    the lancing drive being configured to move the lancet via the holder from the first position to the second position to apply tensile stress to the forward longitudinal edge of the lancet supply strip.

9. The lancing system as defined in claim 1, wherein the bending mechanism includes at least one bending surface extending obliquely relative to the puncturing direction, wherein one longitudinal edge of the lancet supply strip presses against the bending surface.

10. A cassette system having
    a lancet supply strip with a plurality of lancets, arranged transversely to a lengthwise direction of the lancet supply strip, wherein the lancet supply strip is no longer along the lengthwise direction than crosswise in the lengthwise direction, and a bending mechanism for bending a section of the lancet supply strip in the lengthwise direction of the lancet supply strip and for thereby separating a lancet tip of a lancet from the lancet supply strip when the lancet is moved together with a lancet supply strip by a lancing drive in a puncturing movement.

11. A lancing device for collecting a sample of a body liquid having
    a receptacle for accommodating a lancet supply strip with a plurality of lancets, arranged transversely to a lengthwise direction of the lancet supply strip and provided with a lancet tip for producing a puncturing wound;
    a feed mechanism for transporting a lancet supply strip, placed in the receptacle, to move the lancets of a lancet supply strip one after the other to a puncturing position, wherein the feed mechanism is configured to move the lancet supply strip along the lengthwise direction;
    a lancing drive for causing a lancet, which occupies a puncturing position, to perform a puncturing movement in a direction transverse to the lengthwise direction of the lancet supply strip, said lancing drive being configured for moving the lancet together with the lancet supply strip in the puncturing movement; and
    a bending mechanism for bending a section of the lancet supply strip in the lengthwise direction of the lancet supply strip and for thereby separating a lancet tip of a lancet from the lancet supply strip when the lancet is moved together with the lancet supply strip by the lancing drive in the puncturing movement.

12. The lancing device as defined in claim 11, characterized in that for bending the lancet supply strip the bending mechanism acts on a longitudinal edge of the lancet supply strip.

13. The lancing device as defined in claim 12, characterized in that for bending the lancet supply strip the bending mechanism acts on a longitudinal edge of the lancet supply strip by at least one bending surface extending obliquely to the puncturing direction.

14. The lancing device as defined in claim 12, characterized in that the bending mechanism acts on a longitudinal edge of the lancet supply strip by two bending surfaces, the bending surfaces being arranged at a distance one from the other.

15. The lancing device as defined in claim 11, characterized in that the section of the lancet supply strip to be bent is moved in the puncturing direction for bending.

16. The lancing device as defined in claim 11, characterized in that for performing a puncturing action, the lancing drive moves a section of the lancet supply strip, together with a lancet, in the puncturing direction.

17. The lancing device as defined in claim 11, characterized by a testing facility for examination of a sample of a body liquid which is taken up by applying a partial area of the lancet supply strip, which is bent in lengthwise direction, to a body area in which a puncture wound has been produced.

18. The lancing device as defined in claim 17, characterized in that the action of the bending mechanism on the lancet supply strip is interrupted at the end of a puncturing action, the lancet supply strip is advanced by the feed mechanism, and is then again bent in lengthwise direction by the bending mechanism, and a partial area of the lancet supply strip is applied to the body area in which a puncture wound has been produced.

19. The lancing device as defined in claim 11, characterized in that the lancet supply strip is exchangeably arranged in a receptacle.

20. The lancing device as defined in claim 19, characterized by a strip cassette, arranged exchangeably in the receptacle, that contains the lancet supply strip.

21. The lancing device as defined in claim 20, characterized in that the bending mechanism is attached to the strip cassette.

22. The lancing device as defined in claim 11, characterized in that the bending mechanism is designed in that a lancet, together with the section of the lancet supply strip on which it is carried, is held in a holder of the lancet drive, the holder being arranged transversely offset to the puncturing direction between two guide elements, about which the lancet supply strip is guided, and performing a movement in the puncturing direction during a puncturing action.

23. The lancing device as defined in claim 11, wherein the bending mechanism is integrated into the lancing drive.

24. The lancing device as defined in claim 23, wherein the lancing drive is configured to move the lancet from a first position wherein the section of the lancet supply strip is in an unbent state to a second position wherein the section of the lancet supply strip is bent in the lengthwise direction to separate the lancet tip from the lancet supply strip.

25. The lancing device as defined in claim 24, wherein the lancing drive is configured to exert higher stress on a forward longitudinal edge of the lancet supply strip than on a rear longitudinal edge of the of lancet supply strip.

26. The lancing device as defined in claim 25, wherein the bending mechanism includes
   two guide elements guiding the lancet supply strip,
   a holder arranged offset transversely to the puncturing direction between the two guide elements, the holder being configured to hold the lancet in the puncturing position, and
   the lancing drive being configured to move the lancet via the holder from the first position to the second position to apply tensile stress to the forward longitudinal edge of the lancet supply strip.

27. The lancing device as defined in claim 11, wherein the bending mechanism includes at least one bending surface extending obliquely relative to the puncturing direction, wherein one longitudinal edge of the lancet supply strip presses against the bending surface.

28. A lancing system for collecting samples of body liquid comprising:
   a lancet supply strip with a plurality of lancets, arranged transversely to a lengthwise direction of the lancet supply strip;
   a feed mechanism for transporting the lancet supply strip, placed in a receptacle, to move the lancets of the lancet supply strip one after the other to a puncturing position, wherein the feed mechanism is configured to move the lancet supply strip along the lengthwise direction; and
   a lancing drive for causing a lancet, which occupies the puncturing position, to perform a puncturing movement, wherein the lancing drive is configured to move the lancet from a first position wherein the section of the lancet supply strip is in an unbent state to a second position wherein the section of the lancet supply strip is bent in the lengthwise direction to separate a lancet tip from the lancet supply strip,
   said lancing drive being configured for moving the lancet together with the lancet supply strip in the puncturing movement, whereby the lancet supply strip is bent in the lengthwise direction of the lancet supply strip, and thereby the lancet tip is separated from the lancet supply strip in the puncturing movement.

* * * * *